(12) United States Patent
Mazzeo et al.

(10) Patent No.: US 10,646,604 B2
(45) Date of Patent: May 12, 2020

(54) FLEXIBLE PLASMA APPLICATORS BASED ON FIBROUS LAYERS

(71) Applicants: Rutgers, The State University of New Jersey, New Brunswick, NJ (US); University of Florida Research Foundation, Incorporated, Gainesville, FL (US)

(72) Inventors: Aaron Mazzeo, Dunellen, NJ (US); Jingjin Xie, Piscataway, NJ (US); Qiang Chen, Somerset, NJ (US); Subrata Roy, Gainesville, FL (US)

(73) Assignees: RUTGERS, THE STATE UNIVERSITY OF NEW JERSEY, New Brunswick, NJ (US); UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 421 days.

(21) Appl. No.: 15/425,474

(22) Filed: Feb. 6, 2017

(65) Prior Publication Data
US 2017/0224856 A1 Aug. 10, 2017

Related U.S. Application Data

(60) Provisional application No. 62/291,082, filed on Feb. 4, 2016.

(51) Int. Cl.
*A61L 2/14* (2006.01)
*H05H 1/24* (2006.01)

(52) U.S. Cl.
CPC ............. *A61L 2/14* (2013.01); *H05H 1/2406* (2013.01); *A61L 2202/24* (2013.01); *H05H 2001/2412* (2013.01); *H05H 2245/123* (2013.01); *H05H 2245/125* (2013.01)

(58) Field of Classification Search
CPC ........................................................ A61L 2/14
See application file for complete search history.

(56) References Cited

U.S. PATENT DOCUMENTS

| 8,564,558 B2 * | 10/2013 | Yi | G06F 3/044 178/18.06 |
| 2010/0296977 A1 * | 11/2010 | Hancock | A61L 2/14 422/186 |
| 2014/0186525 A1 * | 7/2014 | Seong | H05K 3/1275 427/123 |
| 2017/0136252 A1 * | 5/2017 | Weltmann | A61N 1/44 |

FOREIGN PATENT DOCUMENTS

CN    201805613    *    4/2011

OTHER PUBLICATIONS

Yu et al. CN 201805613. Apr. 2011. English machine translation. (Year: 2011).*
Mazzeo, et al: "Paper-Based, Capacitive Touch Pads", Advanced Materials, 2012, vol. 24, No. 21, pp. 2850-2856.

* cited by examiner

*Primary Examiner* — Donald R Spamer
(74) *Attorney, Agent, or Firm* — Fox Rothschild LLP

(57) ABSTRACT

Disclosed herein are flexible plasma applicators based on fibrous layers that are capable of rapidly sanitizing a surface via either direct or indirect contact with said surface.

20 Claims, 13 Drawing Sheets

FLEXIBLE PLASMA APPLICATORS BASED ON FIBROUS LAYERS

I. CROSS-REFERENCE TO RELATED APPLICATIONS

This application claims priority under 35 U.S.C. § 119(e) to provisional application No. 62/291,082, filed on Feb. 4, 2016, hereby incorporated by reference in its entirety.

II. BACKGROUND

Healthcare-associated infections (HAIs), also referred to as nosocomial infections, are among the most significant cause of morbidity and mortality in healthcare settings, such as in hospitals, throughout the developed and developing world. At any given time, approximately 7% of hospitalized patients in developed countries, and about 10% of those hospitalized patients in developing countries, will acquire at least one HAI. For example, in 2011, in the United States, approximately 721,800 HAIs were reported in hospitals. Of those approximately 721,800 reported HAIs, approximately 75,000 of those patients died during their hospitalization. Put differently, over approximately 10% of those individuals who were diagnosed with at least one HAI in 2011 in the US died during hospitalization. Furthermore, international public health crises, such as the 2014 West African Ebola virus outbreak, and the rapidly growing number of antibiotic-resistant bacteria, including multi-drug resistant and extensively-drug resistant bacteria, represent a significant area of public health concern worth addressing in a cost-effective manner.

Existing plasma generators are typically capable of sanitizing medical devices and killing microbes in atmospheric conditions. However, these plasma-based generators use rigid components which are not capable of bending or conforming to irregularly shaped objects. This lack of flexibility limits potential use and applications. Furthermore, existing plasma generators are expensive and not ecologically friendly for single use in contaminated or sterile environments. Accordingly, there is a need for flexible, economical plasma-based applicators.

III. SUMMARY OF THE INVENTION

In some embodiments, the present invention comprises a plasma applicator. In some embodiments, the plasma applicator is comprised of a first substrate layer, a second substrate layer, and an adhesive layer. In some embodiments, the first substrate layer and the second substrate layer are comprised of a fibrous base layer and a metallic surface layer. In some embodiments, the fibrous base layer is a natural fibrous base layer. In some embodiments, the adhesive layer binds the fibrous base layer of the first substrate layer to the fibrous base layer of the second substrate layer, wherein the metallic surface layer of the first substrate layer and the metallic surface of the second substrate layer is exposed.

In further embodiments, the plasma applicator of the present invention comprises at least one polymer layer inserted between at least one of the fibrous base layer and the metallic surface layer of the first substrate layer and the fibrous base layer and the metallic surface layer of the second substrate layer.

In further embodiments, the plasma applicator of the present invention comprises a conductive polymer coating layer applied to the exposed metallic surface layer of at least one of the first substrate layer and the second substrate layer.

In some embodiments, the substrate layer is patterned. In some embodiments, the substrate layer is patterned so that the metallic surface layer is honeycombed.

In further embodiments of the invention, the plasma applicator comprises a power source to generate plasma. In some embodiments of the invention, alternating potential is applied to the plasma applicator in an amount between of about 1 kV to about 100 kV, and a frequency greater than 1 kHz. In some embodiments, the plasma applicator generates at least one of surface plasma and volume plasma.

In some embodiments, the present invention is directed to method of disinfecting a surface. In some embodiments, the method comprises directly contacting a surface with a plasma applicator of the present invention. In other embodiments, the method comprises indirectly contacting a surface with a plasma applicator of the present invention. In some embodiments, the method results in near complete disinfection within 120 seconds, within 60 seconds, with 30 seconds, within 20 seconds, within 10 seconds, or within 5 seconds.

In some embodiments, the present invention is directed to a flexible bandage that incorporates a plasma applicator of the present invention.

In some embodiments, the present invention is directed to a device, optionally handheld, that comprises disposable or replaceable plasma applicator inserts.

In some embodiments, the present invention is directed to a touch-based interface incorporating a plasma applicator of the present invention. In some embodiments, the touch-based interface is a capacitive touch-based interface.

In some embodiments, the present invention is directed to a garment that comprises a plasma applicator of the present invention.

In some embodiments, the present invention is directed to packaging that comprises a plasma applicator of the present invention.

IV. DESCRIPTION OF THE DRAWINGS

V. DETAILED DESCRIPTION OF THE INVENTION

A. Healthcare-Associated Infections/Nosocomial Infections

There are numerous potential underlying causes for HAIs. However, a significant number of HAIs are directly attributable to improper or insufficient sanitation and/or disinfection practices at healthcare settings, such as in a hospital. According to the World Health Organization (WHO), an estimated 40% of HAIs are caused by poor hand hygiene. This may result in cross-contamination and spread of infectious agents, including both pathogenic agents such as *E. coli* and opportunistic agents, such as fungus or yeast, or opportunistic bacteria such as *Clostridium difficile* (*C. difficile*). Many HAIs are caused by drug-resistant bacteria, i.e. methicillin-resistant *Staphylococcus aureus* (MRSA) and vancomycin-resistant enterococci (VRE). A significant number of bacterial HAIs are Gram-negative bacteria, and a significant number of Gram-negative bacterial infections are antibiotic resistant. Gram-negative bacterial infections that are common in hospital settings include bacterial pneumonia, bloodstream infections, wound or surgical site infections, and bacterial meningitis. In general, invasive surgery carries a much higher risk than non-invasive surgical procedures in acquiring HAIs.

B. Plasma Applicators i. Plasma Sanitation

"Plasma" is defined herein as the fundamental state of matter characterized by a quasi-neutral collection of electrons, positive ions, and neutrals capable of collective behavior. Plasma is further characterized by a lack of molecular bonds. The presence of a significant number of charge carriers renders plasma electrically conductive so that it responds strongly to magnetic fields. Plasma does not have a definite shape or volume, like gasses. However, unlike gases, plasma may form structures such as filaments, beams, and layers under the influence of a magnetic field. Sanitation by plasma discharge generally occurs through three synergistic mechanisms: free radical interactions, UV/VUV radiative effects, and volatilization.

ii. Plasma Applicator Structure and Construction

The plasma applicators of the present invention utilize dielectric barrier discharge (DBD) technology that allows for plasma discharge to reach material surface. DBD is defined herein as is the gas-discharge between two electrodes, separated by one or more dielectric layers and a gas-filled gap. The plasma applicators of the present invention operate at atmospheric pressure, room temperature, at an alternating current (AC) voltage of about 1 kV to about 100 kV, and a frequency greater than 1 kHz, for example from about 2 kHz to about 10 kHz, although no set frequency is required over 1 kHz.

Figure 1:
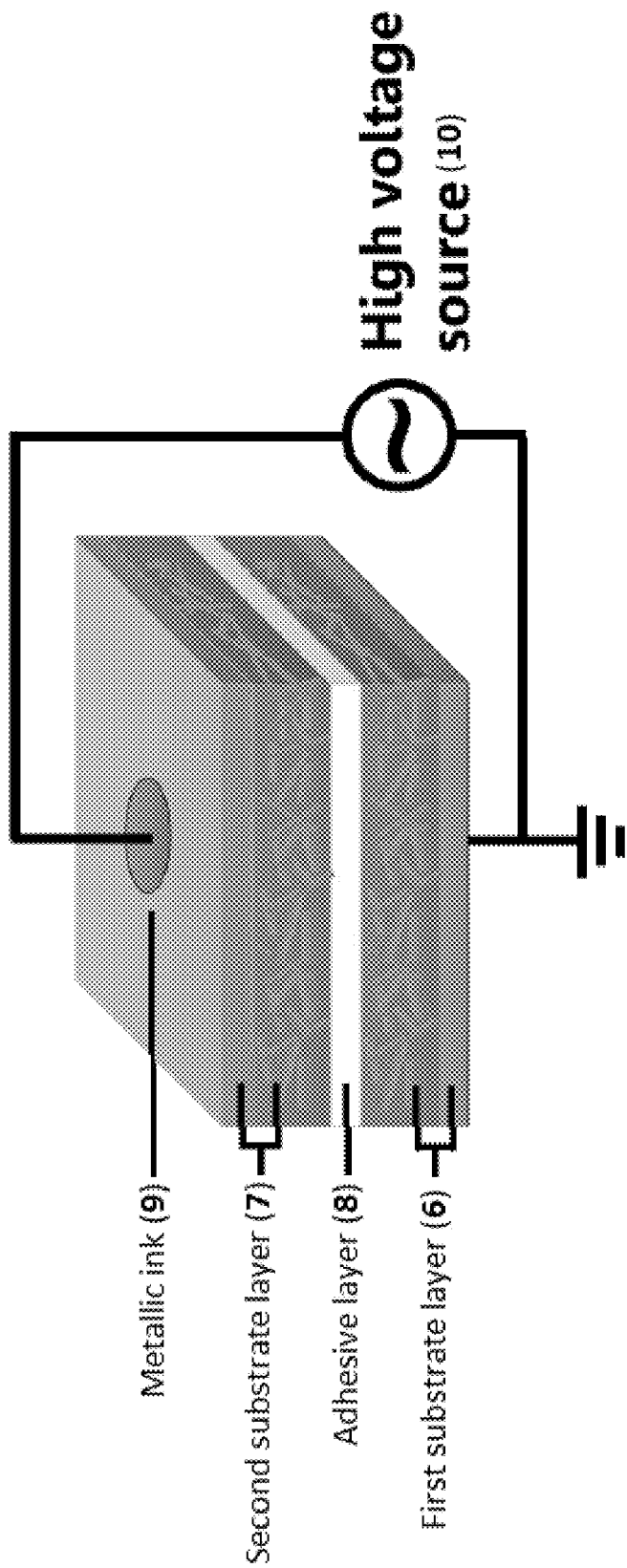
FIG. 1 represents an exemplary plasma applicator utilizing dielectric barrier discharge (DBD) technology of the present invention.
Figure 2:
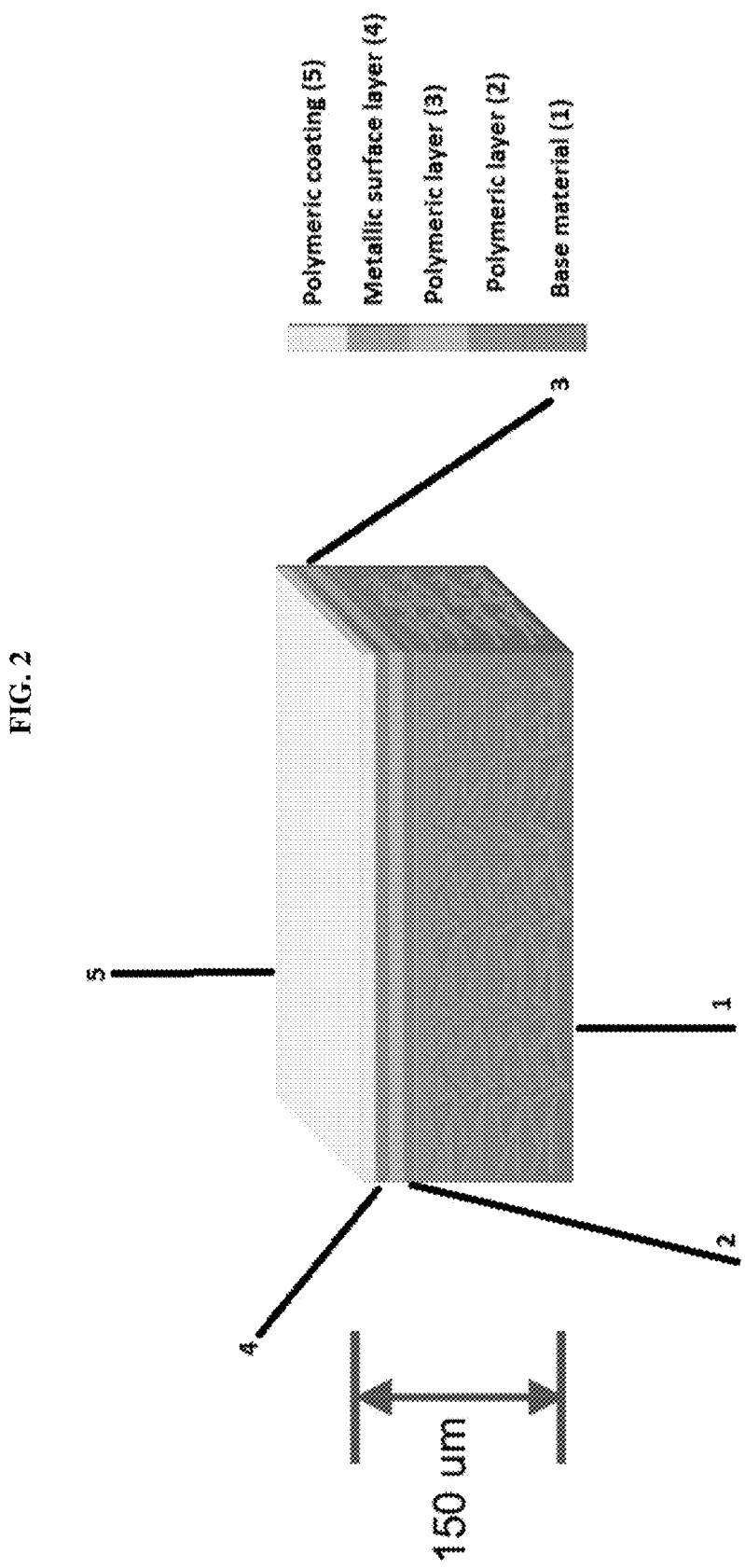
FIG. 2 represents an exemplary structure of the substrate layers, with optional interior polymeric layers and optional polymeric coating represented.

The plasma applicators are organized in a "two-layer" configuration, comprising a first substrate layer 6, a second substrate layer 7, and an interior adhesive layer 8 that binds the first substrate to the second substrate layer (FIG. 1). The thickness of the substrate layers 6, 7 may be variable, but optimally are around 150 µm in thickness (FIG. 2). The thickness of the adhesive layer may be variable, but optimally is around 30 µm in thickness. The substrate layers may be thicker or thinner, so long as the electric potential across the two electrodes remains high enough to induce dielectric discharge and so long as the high electrical potential below the dielectric strength of the substrate. The overall thickness of the plasma applicators may be up to about 2 mm in thickness, with each substrate layer 6, 7 being up to about 1 mm. The substrate layers are comprised of a base material comprising fibrous material. The fibrous material may be either natural fibrous material or synthetic fibrous material, e.g. rayon or woven synthetic polyester. Natural fibrous material as defined herein includes any base material derived from natural sources, including but not limited to both woven and non-woven fiber substrates, e.g. non-woven cellulosic fiber substrates such as paper, pressed pulp, and other related materials, and other materials such as a scrim or scrim layer, leather, or textiles. Cellulose-based paper is of particular interest as a base material, as it is a flexible, renewable, and biodegradable material. Cellulose-based paper has tunable porosity to allow gases to permeate its bulk volume, and is capable of handling temperatures of up to 250° C. These properties make cellulose-based paper suitable as a base material for the plasma applicators of the present invention as the permeability of cellulose-based paper allows the flow of gas through the substrate to provide fuel for the plasma and to cool the cellulose based paper with forced convection. Accordingly, in some embodiments, the base material for the first substrate layer and/or the second substrate layer of the plasma applicators of the present invention comprises cellulose-based paper.

The first substrate layer 6 and the second substrate layer 7 are assembled as follows (FIG. 2). Optionally, at least one polymeric layer 2, 3 is layered on top of the base material 1, followed by a metallic surface layer 4, and optional polymeric coating 5. The optional at least one polymeric layer(s) 2, 3 are preferably non-conductive and serve to ensure the stability of the overall plasma applicator. The optional polymeric coating 5 serves a similar purpose, in providing improved structural stability and likewise is preferably non-conductive.

Preferably, the metallic surface layer 4 is comprised of vacuum evaporated aluminum, but any conductive metal is appropriate. The first 6 and second 7 substrate layers are oriented in the plasma applicators such that the adhesive layer 8 binds to the base material 1 of each substrate layer 6, 7, thus exposing the metallic surface layers 4 (or the optional polymeric coating 5) on the outer surfaces of the plasma applicators. The metallic surface layers 4 (with optional polymeric coating 5) serve as electrodes, while the base material 1 and adhesive layer 8 serve as an insulating dielectric barrier. Optionally, a conductive layer of metallic ink 9, e.g. conductive silver ink, or other similar substance is placed on the contact points of the exposed metallic surface layers 4 (or optional polymeric coating 5) of the plasma applicator. The plasma applicator may further comprise an additional porous insulation layer between the first substrate layer 6 and the second substrate layer 7, which may render the plasma applicator especially suitable for use as a bandage for skin treatment. A bandage for skin treatment may additionally comprise a non-conductive spacer placed on an exposed surface of either the first substrate layer 6 or on an exposed surface of the second substrate layer 7, whichever layer would be coming in contact with the skin. The non-conductive spacer may be thermally insulating, and may be electrically insulating. The plasma applicators of the present invention are capable of generating both surface plasma and volume plasma.

Figure 3:
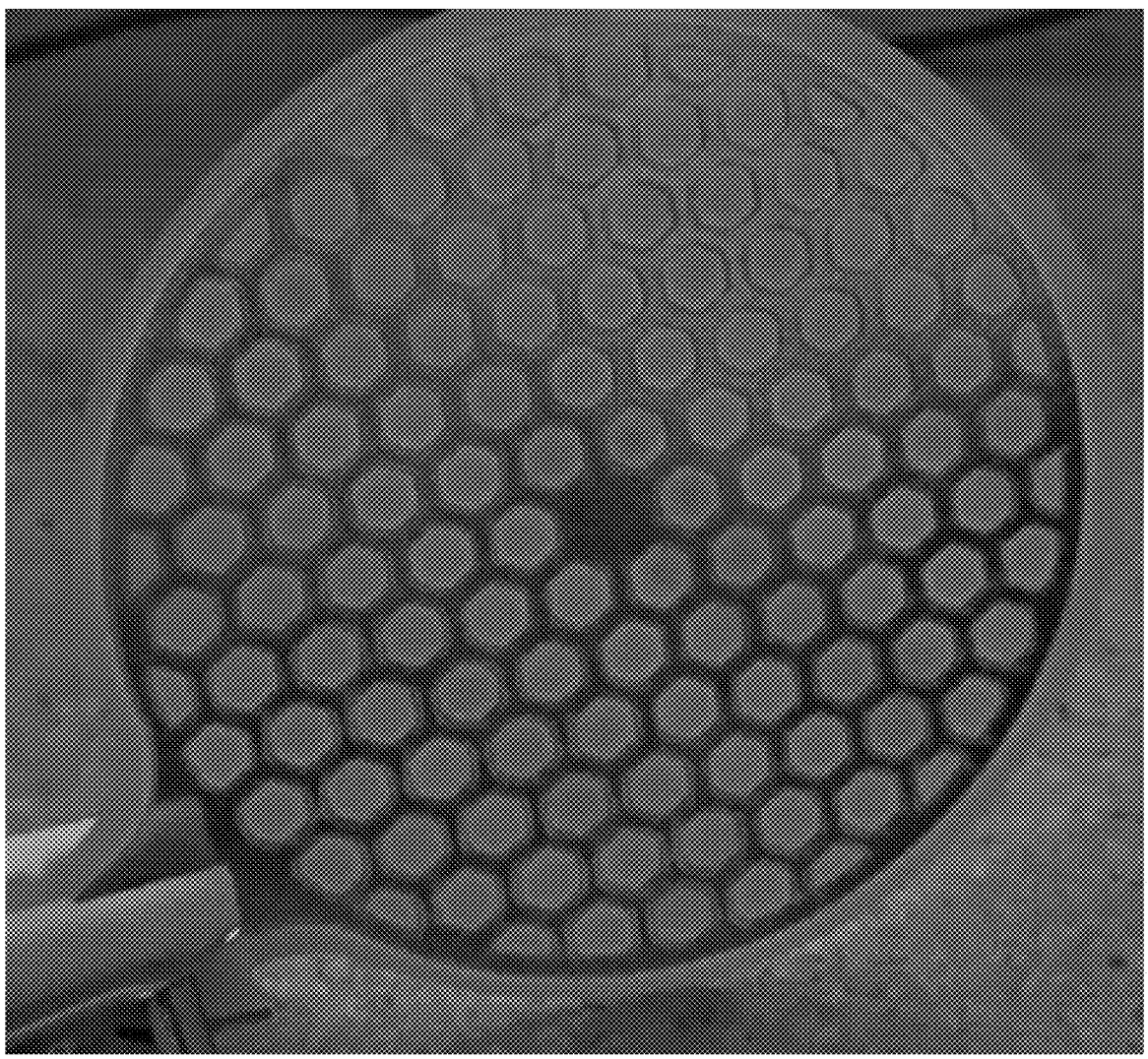
FIG. 3 represents an exemplary structure of a plasma applicator in a circular configuration and portraying an optional "honeycomb" design.

One or both of the metallic surface layers 4 of the substrate layer(s) 6, 7 may be patterned, for example, on one or both of the surface(s) of the metallic surface layer(s) 4. Additionally, one or both of the substrate layer(s) 6, 7 may be patterned such that the exposed metallic surface layers are fabricated to on an overall shape or design, for example but not necessarily a "honeycomb" design, thus partially exposing the base material 1 where the metallic surface layer 4 is cut away (FIG. 3). The patterning may be achieved, e.g., by laser etching and/or laser engraving, by mechanical means, such as by hole punching, or by chemical reaction, e.g. with acid. The goal of such patterning may be to increase air flow, which can lead to an increased generation of plasma, including surface plasma and volume plasma.

To generate both surface and volume plasma, a high voltage source 10 is applied to the contact points on the surfaces of the DBD. For example, to produce plasma, the present invention utilized sinusoidal signals with frequencies ranging from about 1 kHz to about 8 kHz and peak-to-peak voltages $V_{p-p}$ ranging from about ±0.5 V to about ±5 V using a function generator (4011A, BK Precision). This signal was amplified using a high-voltage amplifier (Model 10/10, TREK) with a gain of 1000 to output a high oscillating potential $V_{p-p}$ ranging from ±500 V to ±5 kV. The generation of plasma was frequency dependent. While not wishing to be bound by theory, this suggests the existence of an optimal frequency at a given electrical potential to generate uniform coverage of plasma.

Figure 4:
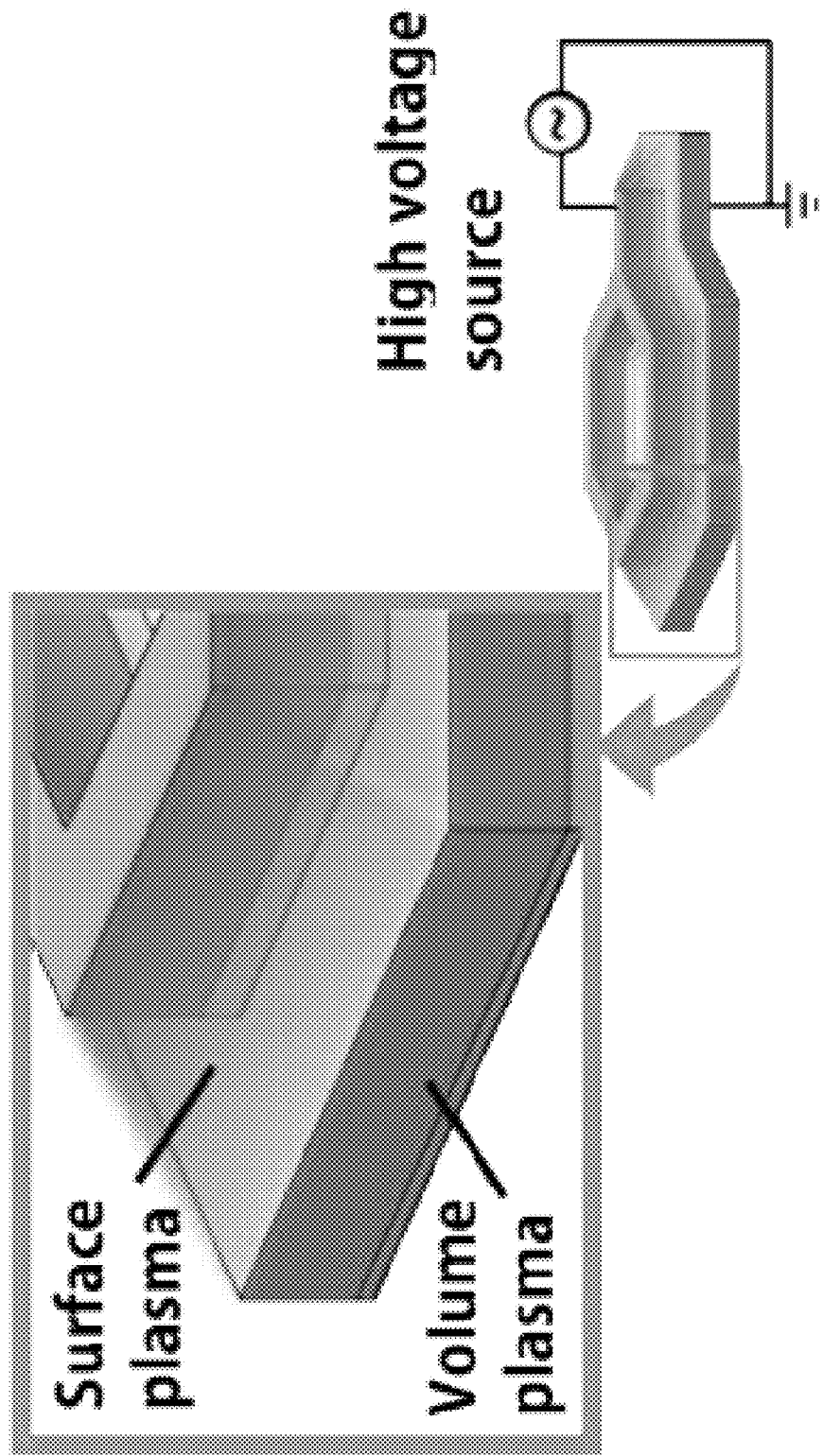
FIG. 4 represents the typical geometry and location of both volume plasma and surface plasma in a plasma applicator.

Generally, DBD can produce two types of plasma, volume plasma and surface plasma, depending on the configuration of the DBD. In each instance, the DBD is comprised of one or more dielectric insulators sandwiched by electrodes, however volume plasma is ordinarily generated when there is a discharge gap between the two electrodes that is large enough to contain an adequate amount of air. In some circumstances where the discharge gap is major, volume plasma is the primary discharge, i.e. the major discharge is between the two electrodes. If however, the gap between the electrodes is very small or non-existent, surface plasma is generated as the discharge will occur on the surfaces around the electrodes. The typical geometry and location of both volume plasma and surface plasma is illustrated in FIG. 4.

Surprisingly however, the present invention may be capable of generating both surface and volume plasma, a distinct advantage that directly arises from the use of fibrous base material. Such base material may be naturally porous, especially in the case of natural fibrous material, opposed to non-porous polymer base materials, and such porous materials may allow for an adequate amount of air to fill in small gaps between the two electrodes to generate volume plasma in addition to surface plasma that is generated. The capability of generating both surface and volume plasma gives rise to the ability to sanitize not only the objects closed to a sanitizer via surface plasma, but also the plasma applicator itself via volume plasma. The raw material comprising the base layer, for example but not limited to cellulose-based paper, may contain microbes inside its porous, fibrous structure. With the presence of volume plasma, it is possible to deactivate these residing microbes.

iii. Advantages/Methods of Use

The plasma applicators of the present invention have a number of advantages, both technical and economical, over the current devices and methods, including preventing HAIs. Low-cost plasma applicators using, for example, cellulose-based paper as a base material may reduce the rate of morbidity and mortality resulting from nosocomial infections in healthcare facilities. However, the use of the plasma applicators of the present invention is not limited to such use. The field of uses for the plasma applicators of the present invention is broad, and may be applied in any circumstance in which disinfection is desired. For example, the plasma applicators of the present invention may be used to disinfect surfaces, sanitize food during food processing, and be applied to a wound for treatment, for example but not necessarily as a bandage or wound dressing. The plasma applicators may also be utilized to disinfect electronic equipment. In particular, the plasma applicators of the present invention are well-suited for chronic or non-healing wounds that are susceptible to infection, e.g. ulcers, including venous and arterial ulcers, diabetic ulcers, and pressure ulcers, or for other openings, such as stomas. The plasma applicators of the present invention may be especially well-suited for those individuals who are immunocompromised. The plasma applicators of the present invention may also be utilized with capacitive touch-technology to create self-sanitizing touchpads.

The plasma applicators of the present invention may be utilized to disinfect either via direct contact with a surface or indirect contact with a surface. Direct contact with a surface may be utilized, for example, in a wound dressing or bandage, or may be used in other settings such as sanitation of equipment. Indirect contact may have a number of uses, including passing objects through a volume or space in which plasma is being generated for sanitation and/or preservation purposes, such as foodstuffs or equipment, or for any other surface or object in which direct contact would be undesirable. Non-contact or indirect contact may occur at a distance from about 0.5 cm to about 1.0 cm from the surface to be sanitized although distances as close to about 0 mm and as far as about 3 cm from the surface would be acceptable.

The plasma applicators of the present invention effect surprisingly rapid surface sanitation—sanitation is seen within seconds in many circumstances. The plasma applicators of the present invention may achieve near complete surface sanitation via direct contact in as little as 5 seconds in certain circumstances, and no more than 60 seconds. For indirect contact, the plasma applicators of the present invention may achieve near complete surface sanitation in as little as 10 seconds, and no more than 60 seconds.

The plasma applicators of the present invention are environmentally friendly. They are disposable and bio-degradable as the base material is made from fibrous material (e.g. cellulose-based paper) rather than the non-fibrous polymer-based dielectric materials found in other devices. Because the base material is made from fibrous material, and because the thickness of the substrate layers are limited to a size range of about 100 μm to about 2 mm, the plasma applicators of the present invention are non-rigid and flexible, meaning that they can be arranged in a wide number of shapes, contoured to a wide range of surfaces, and adapted to a wide range of utilities. Particularly for natural fibrous materials, especially cellulose-based paper, the plasma applicators may represent a significantly more economical solution than those employing more expensive synthetic polymer-based dielectric materials, yet exhibit the same or enhanced disinfectant capacity The plasma applicators of the present invention may come in variable shapes and size that can be suited to any particular need, as opposed to a fixed size, and may be portable, i.e. handheld, plasma-based bandages. This is because the plasma applicators of the present invention are designed from lightweight, thin, and flexible adhered substrate layers. Related to this, the fabrication process of the plasma applicators of the present invention is scalable. The plasma applicators of the present invention are customizable in shape, size, material, and width. Due to the relatively simple construction of the plasma applicators, the plasma applicators of the present invention represent economical and affordable solutions for disease control, inside hospital settings and outside of such, i.e. for treatment of food-borne infections, or for application in wound treatment. The plasma applicators of the present invention are non-corrosive. They do not contain bleach, alcohols, or other harsh chemical oxidizers or disinfectants, and do not rely on ethylene oxide. The plasma applicators of the present invention do not rely on potentially dangerous gamma radiation for disinfection, nor do they rely on electron beam sanitation employed by large, costly medical equipment.

The plasma applicators of the present invention are scalable. Notably, electrical resistance scaled with the size of the plasma applicators, consistent with previously reported methods of decreasing the frequency of applied voltage to generate plasma through resistive barrier discharge. For example, the frequency of excitation for a plasma applicator of 400 mm×276 mm was 100 Hz at a voltage $V_{p-p}$ of ±3 kV.

iv. Self-Sanitizing Touchpad

One particular use of the plasma applicators of the present invention is coupled with capacitive touch technology. A capacitive touch input, such as a touchpad, may be attached to a plasma applicator of the present invention. When contact is made with the capacitive touch input, the plasma applicator may be activated. The touch input may be placed directly on an exposed surface of a plasma applicator of the present invention, or a plasma applicator of the present invention may be incorporated into a surface comprising a capacitive touchpad. Accordingly, in such embodiments of the present invention, when the capacitive touchpad is touched, the plasma generator is activated and the touchpad is self-sanitized. This would address a significant concern of touch-based interfaces and surfaces as a fomite, especially in a healthcare setting or other setting where contamination is a concern. Self-sanitizing touchpads are examined in Example 4 infra.

v. Handheld Device

Another particular use of the plasma applicators of the present invention is in a device that contains inserts, optionally replaceable or disposable, comprising the plasma applicators as disclosed herein, a housed electricity source, e.g. a battery, optionally rechargeable, and a handle or other means for a user to hold. Optionally, the electricity source could be stored in the handle. A user would be able to activate the plasma applicator via, e.g, a button, switch, or other on/off means. Alternatively, the handheld device may utilize the touchpad technology disclosed herein, including the self-sanitizing touchpad. Such handheld devices would be especially attractive for home use or private consumers, and is achievable due to the low cost of the materials involved in constructing the plasma applicators of the present invention.

vii. Disposable Garments

Yet another particular use of the plasma applicators of the present invention would be in disposable garments, e.g. paper-based disposable garments. Protective garments are examined in Example 5 infra.

viii. Kirigami-Based Applications

Kirigami is a variation of origami that includes cutting of paper rather than folding the paper. Kirigami typically starts with a folded base which is subsequently unfolded. Cuts are then opened and flattened to create the finished kirigami product. Kirigami products are typically symmetrical and employ a degree of flexibility that may be advantageous for incorporation in the plasma applicators of the present invention. Kirigami-like plasma generators may be especially useful for creating conformable electronics that require stretching or bending about more than one axis. Kirigami-based applications are examined in Example 6 infra.

ix. Package Based Applications

The plasma applicators of the present invention may be included in packaging, such as packaging for foodstuffs. In such embodiments, the plasma applicators would be included on an interior surface of the packaging, so that the plasma applicators are facing the materials, e.g. foodstuffs or other articles to be sanitized. The exterior of the packaging could optionally contain contact points that connect to a metal surface of the plasma applicators contained within the packaging, such contacts would be capable of coming in contact with a high voltage source so as to activate the plasma applicators without actually having to open the packaging up, allowing for rapid disinfection of the materials within the packaging without disturbing the integrity of the overall packaging. The plasma applicators contained with the packaging may also contain a non-conductive spacer, similar to the bandages, that may protect the contents of the package from coming in direct contact with the plasma applicators.

x. Equivalents

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference in their entireties.

As used herein and in the appended claims, the singular forms "a", "and" and "the" include plural references unless the context clearly dictates otherwise.

The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values.

Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following non-limiting examples serve to further illustrate the present invention.

VI. EXAMPLES

1. Ozone Generation

In order to demonstrate the plasma generation of the plasma applicators, the corresponding ozone level ($O_3$) generated by the plasma applicators of the present invention was measured in parts-per-million (ppm) over time and displayed in TABLE 1 below. The plasma applicators were constructed according to the structure set forth in exemplary FIG. 1 and FIG. 2, with each substrate layer constructed with a base layer comprising paper, two successive polymeric layers on top of the base layer, vacuum evaporated aluminum comprising the metallic surface layer on top of the second polymeric layer, and a layer of polymeric coating covering the metallic surface layer. The plasma applicator was constructed according to FIG. 1, with an adhesive layer binding the base layers of both substrate layers to each other such that the conductive polymeric-coated metallic surface layers were exposed. Conductive silver ink was placed on the contact points for the plasma applicator. The level of UV-C radiation detected was 1.9 mW/cm$^2$/nm, the surface temperature was reported as 60° C. within 60 seconds of activation, and a high level of ozone (approximately 13 ppm within 60 seconds of activation) was observed.

TABLE 1

Ozone concentration generated by plasma applicator.

| Time (s) | Ozone Concentration (ppm) |
|---|---|
| 5 | 5.56 |
| 10 | 7.23 |
| 20 | 9.81 |
| 30 | 8.97 |
| 60 | 13.53 |
| 120 | 27.34 |

2. Non-Contact (Indirect Contact) Experiments

Non-contact experiments were carried out with the plasma applicators of the present invention. In these experiments, the plasma applicators were designed according to the criteria set forth as described in section IV(B)(ii) above, with both substrate layers designed with laser-etched "honeycomb" shaped metallic surface layers. The plasma applicators were constructed according to the structure set forth in exemplary FIG. 1 and FIG. 2, with each substrate layer constructed with a base layer comprising paper, two successive polymeric layers on top of the base layer, vacuum evaporated aluminum comprising the metallic surface layer on top of the second polymeric layer, and a layer of polymeric coating covering the metallic surface layer. The plasma applicator was constructed according to FIG. 1, with an adhesive layer binding the base layers of both substrate layers to each other such that the conductive polymeric-coated metallic surface layers were exposed. Conductive silver ink was placed on the contact points for the plasma applicator. Each plasma applicator had a diameter of 90 mm, matching the inner diameter of the lid of a Petri dish. By attaching the plasma applicator to the inner surface of the Petri dish lid, the plasma applicator was not directly contacted, which avoided unintentional contamination. When closed, the surface of the plasma applicator was 10 mm away from the surface of the media. For both experiments 1 and 2, the voltage applied to the plasma applicator was 6.3 kV and the frequency was set to 2 kHz.

For both Examples 2 (indirect contact) and 3 (direct contact), *S. cerevisiae* strain AH109 (Clontech Laboratories, Inc.) and *E coli* strain TOP 10 (Invitrogen) served as samples of fungus and bacteria. AH109 is a yeast strain usually used for two-hybrid screening and TOP10 is an ideal bacterial strain for high-efficiency cloning and plasmid propagation. AH109 and TOP10 were cultured with yeast extract peptone dextrose (YEPD) medium and lysogeny broth (LB) respectively. The YEPD broth contained 1% (m/v) yeast extract (Difco), 2% (m/v) peptone (Sigma-Aldrich Corp.), 2% (m/v) dextrose (VWR international), with the remainder being distilled water. The YEPD solid medium contained 0.3% (m/v) yeast extract, 1% (m/v) peptone, 1% (m/v) dextrose, 2% (m/v) agar (Difco), with the remainder being distilled water. LB was prepared with the dehydrated culture medium of Luria-Bertani (Difco) and proper hydration with distilled water. The preferred LB medium contained 2.5% (m/v) LB powder, the rest being distilled water. The LB solid medium contained 2.5% (m/v) LB powder, 1.5% (m/v) agar, the rest being distilled water. Autoclavation of all media lasted for 20 minutes at 121° C. For both the solid media of YEPD and LB, 25 mL of media was contained in each Petri dish. AH109 and TOP10 was cultured in 150 RPM in an orbital incubator shaker (Model 3527, Lab-Line Instrumentations Inc.) for 24 hours at room temperature. The microbes were collected by centrifuging (Clinical 100, VWR International) the cultures at 4000 RMP for 5 minutes. Both AH109 and TOP10 cells were in suspension with sanitized distilled water. To determine the concentration of AH109 and TOP10 in the suspension, a spectrophotometer (Genesys 10s UV-VIS, Thermo Scientific) was utilized to measure the $OD_{600}$. The measured $OD_{600}$ of AH109 and TOP10 were 1.037 and 0.867 respectively, indicating concentrations of approximately $6.22 \times 10^7$ cells/mL and $6.94 \times 10^8$ cells/mL respectively. The concentrations were diluted to $2.07 \times 10^3$ cells/mL and $2.50 \times 10^4$ cells/mL respectively.

A. Experiment 1-*S. cerevisiae*

Figure 5A:
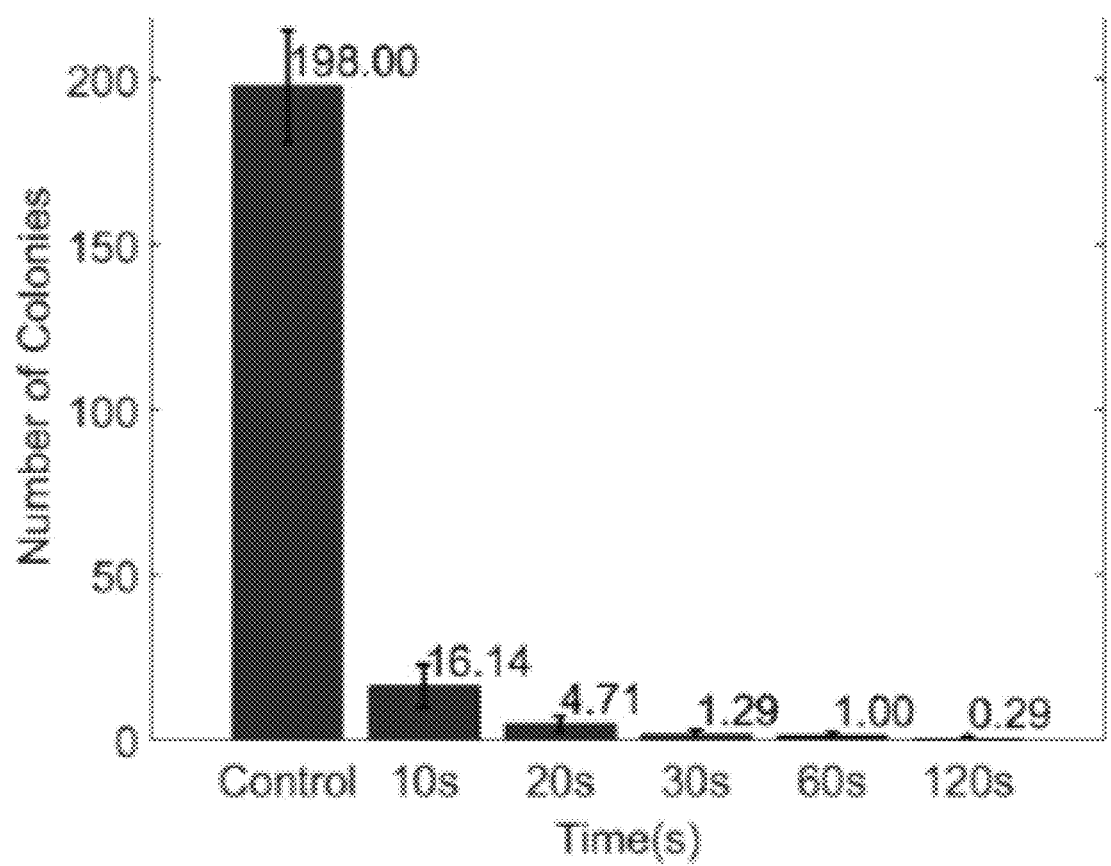
FIG. 5A represents average colony counts at 24 hours for the six Saccharomyces cerevisiae (S. cerevisiae) indirect contact experimental groups.
Figure 5B:
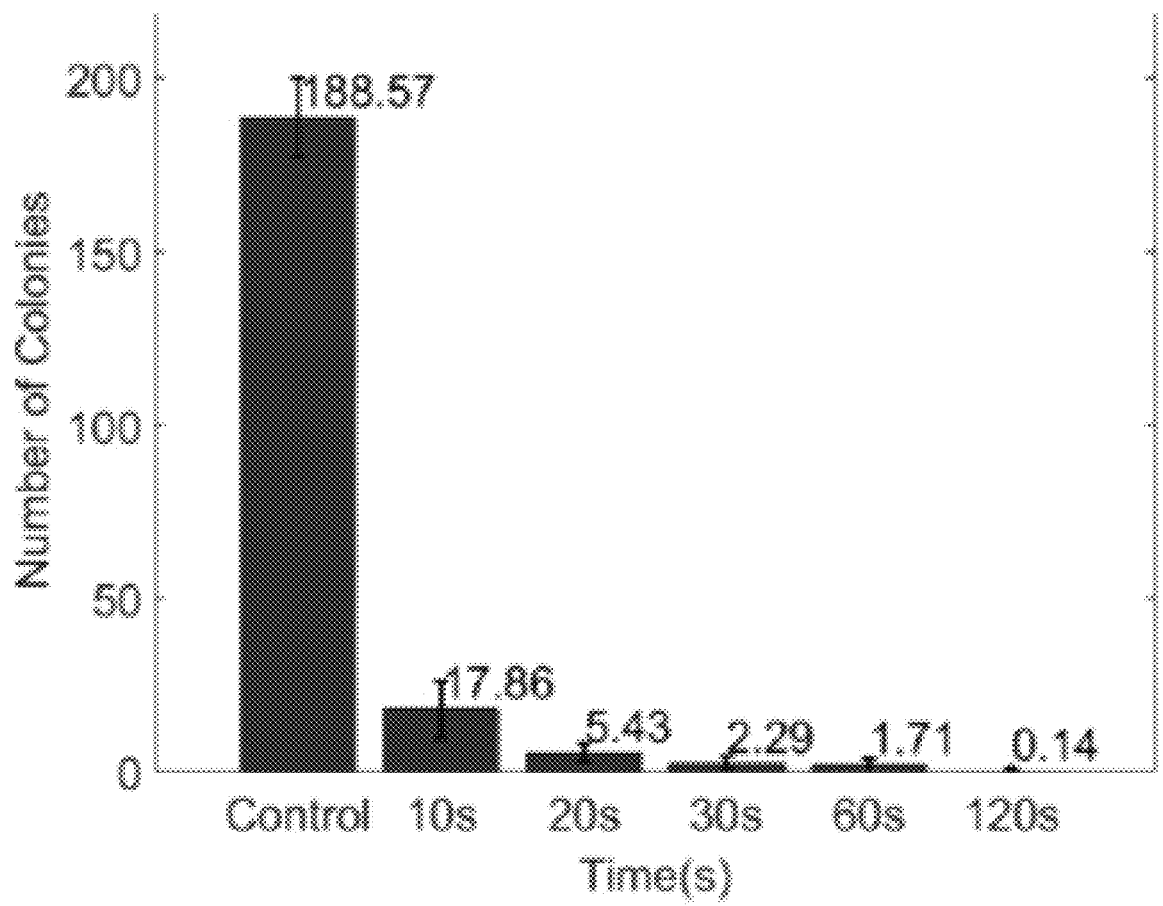
FIG. 5B represents average colony counts at 48 hours for the six S. cerevisiae indirect contact experimental groups.

The plasma applicator was pre-sanitized by standard UV sanitation procedures. The plasma applicator as described was placed in a covered petri dish at a distance of 10 mm from the surface of a medium consisting of yeast extract peptone dextrose (YEPD). The test target for Experiment 1 was *S. cerevisiae* at a concentration of $3.6 \times 10^4$ unit/mL. This was achieved by inoculating 100 μL of *S. cerevisiae* cell suspensions on the YEPD media. The lead of the circular applicator ran through the gap between the lid and the Petri dish to an AC input with a frequency of 2 kHz and a peak-peak voltage of ±3.15 Kv. There was a total of 6 testing groups (5+1 control), with each testing group corresponding to a different length of time for which plasma was generated (i.e the plasma applicator was active): 10 seconds, 20 seconds, 30 seconds, 60 seconds, and 120 seconds. The number of resultant colonies were recorded for each testing group at 24 hours and 48 hours. The experiment was repeated seven times for each group and the results were averaged and displayed in FIG. 5A (24 hours) and FIG. 5B (48 hours).

B. Experiment 2-*E. coli*

Figure 6:
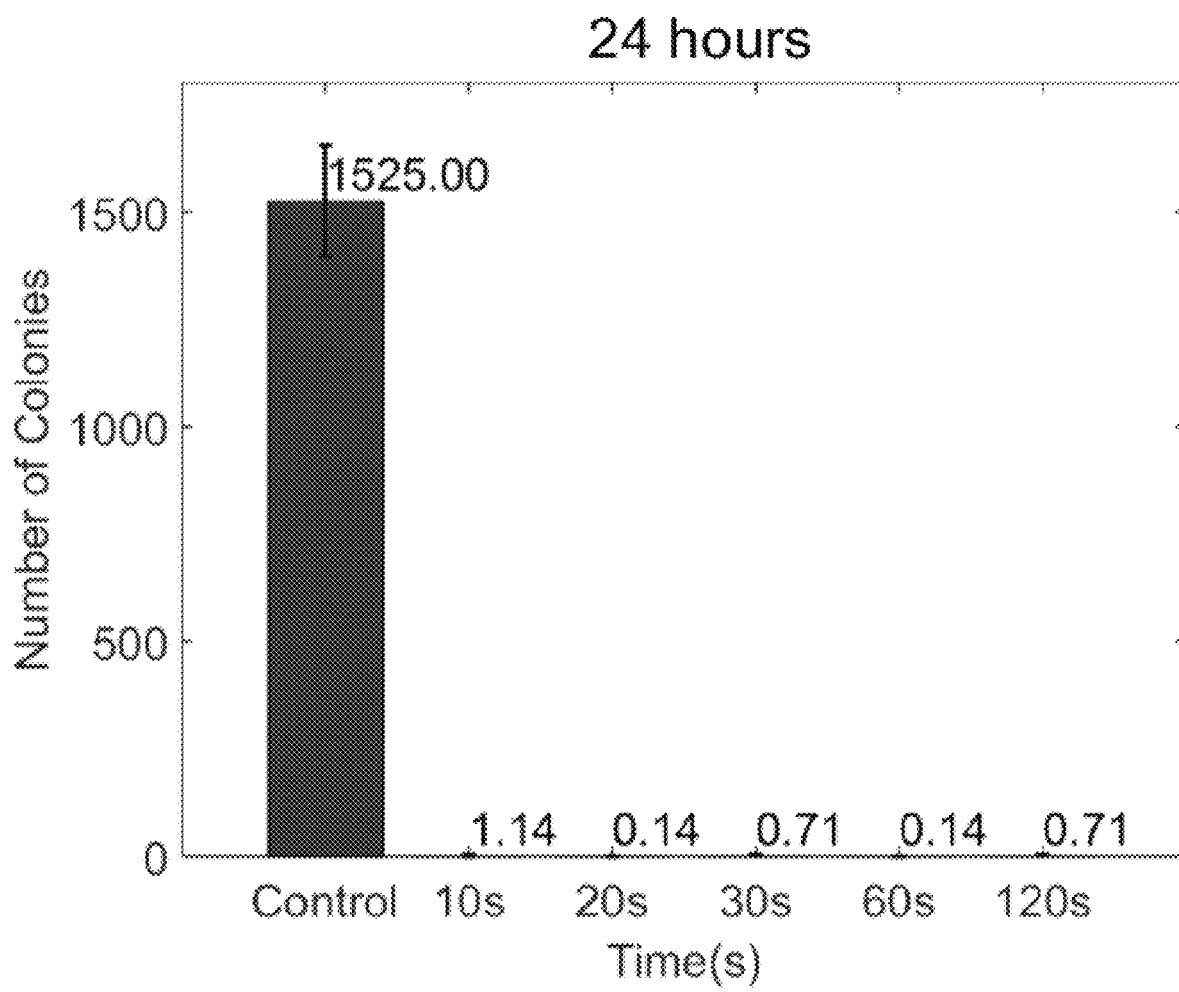
FIG. 6 represents average colony counts at 24 hours for the six Escherichia coli (E. coli) indirect contact experimental groups.

The plasma applicator was pre-sanitized by standard UV sanitation procedures. The plasma applicator as described was placed in a covered petri dish at a distance of 10 mm from the surface of a medium consisting of lysogeny broth (LB). The test target for Experiment 2 was *E. coli* at a concentration of $3.6 \times 10^4$ unit/mL. This was achieved by inoculating 100 μL of *E. coli* cell suspensions on the LB media. The lead of the circular applicator ran through the gap between the lid and the Petri dish to an AC input with a frequency of 2 kHz and a peak-peak voltage of ±3.15 kV. There was a total of 6 testing groups (5+1 control), with each testing group corresponding to a different length of time for which plasma was generated (i.e the plasma applicator was active): 10 seconds, 20 seconds, 30 seconds, 60 seconds, and 120 seconds. The number of resultant colonies were recorded for each testing group at 24 hours. The experiment was repeated seven times for each group and the results were averaged and displayed in FIG. 6.

C. Results

After 10 seconds of active treatment, the mean number of colonies decreased to 16.14, signifying an inactivation rate of 91.85%. After 20 seconds and 30 seconds of treatment, the inactivation rate for *S. cerevisiae* became 97.89% and 99.34% respectively. With respect to *E. coli*, within 10 seconds of treatment the resulting inactivation rate was as high as 99.93%. Treatments longer than 10 seconds resulted in an average of less than 1 remaining colony, representing efficiencies greater than 99%. The results thus indicate efficiencies as high as 99% with treatment times of only 30 seconds.

The decimal reduction time, or D-value, is the time required at a given condition (e.g. temperature) or set of conditions to kill 90% (1 log) of exposed microorganisms in a sample. Calculation of D-value is set forth in the equation below:

$$D\text{-value}=t/[\log(N_0)-\log(N_t)]$$

wherein $N_0$ is the initial population and $N_t$ is the population at the end of the test.

Based on the results of experiments 1 and 2 of Example 2 (indirect contact), the calculated D-values for both *S cerevisiae* and *E. coli* were less than 10 seconds, illustrating the surprising efficacy of the plasma applicators in an indirect contact scenario.

3. Direct Contact Experiments

Direct contact experiments were carried out with the plasma applicators of the present invention. In these experiments, the plasma applicators were designed according to the criteria set forth as described in section IV(B)(ii) above, with both substrate layers designed with laser-etched "honeycomb" shaped metallic surface layers. The plasma applicators were constructed according to the structure set forth in exemplary FIG. 1 and FIG. 2, with each substrate layer constructed with a base layer comprising paper, two successive polymeric layers on top of the base layer, vacuum evaporated aluminum comprising the metallic surface layer on top of the second polymeric layer, and a layer of conductive polymeric coating covering the metallic surface layer. The plasma applicator was constructed according to FIG. 1, with an adhesive layer binding the base layers of both substrate layers to each other such that the conductive polymeric-coated metallic surface layers were exposed. Conductive silver ink was placed on the contact points for the plasma applicator.

These experiments were carried out in an experimental setup to simulate a human sneeze and test the efficacy of the plasma applicators of the present invention. Experiments 1 and 2 pre-sanitized the plasma applicator with UV sanitation techniques prior to simulation of a human sneeze, while experiments 3 and 4 did not pre-sanitize the plasma applicator. Hence, experiments 3 and 4 illustrate not only the ability of the plasma applicators to sanitize the microbes in the simulated human sneeze, but also unknown microbes on the surface of the non-sanitized plasma applicators.

For experiments 1, 2, 3, and 4, a human sneeze was simulated through use of the Nordson EFD Precision dispensing system (Performus II, Nordson EFD), a droplet dispensing machine which can precisely control the amount of liquid it dispenses each time. Each simulated sneeze contained either diluted *S. cerevisiae* at concentration of $3.5 \times 10^8$ unit/mL (experiments 1 and 3) or *E. coli* at a concentration of $3.6 \times 10^8$ unit/mL (2 and 4). Using a gauge pressure of 11 psi and a dispensing time of 50 μs, an intranasal drug delivery device (MAD Nasal, LMA) atomized a liquid suspension of *S. cerevisiae* (experiments 1 and 3) or *E. coli* (experiments 2 and 4) onto the plasma applicators. The simulated sneeze was dropped directly onto the surface of the plasma applicator, which for all 4 experiments was repeated for plasma generation times of 0 seconds (Control), 5, 10, 20, 30 and 60 seconds. A blank control (BC) was also used, which contained the same type of paper-based plasma applicator but was not activated. After plasma generation, the plasma applicator came in direct contact with a petri dish which were then incubated at 30° C. for 48 hours to observe growth.

A. Experiment 1-*S. cerevisiae*

Figure 7:
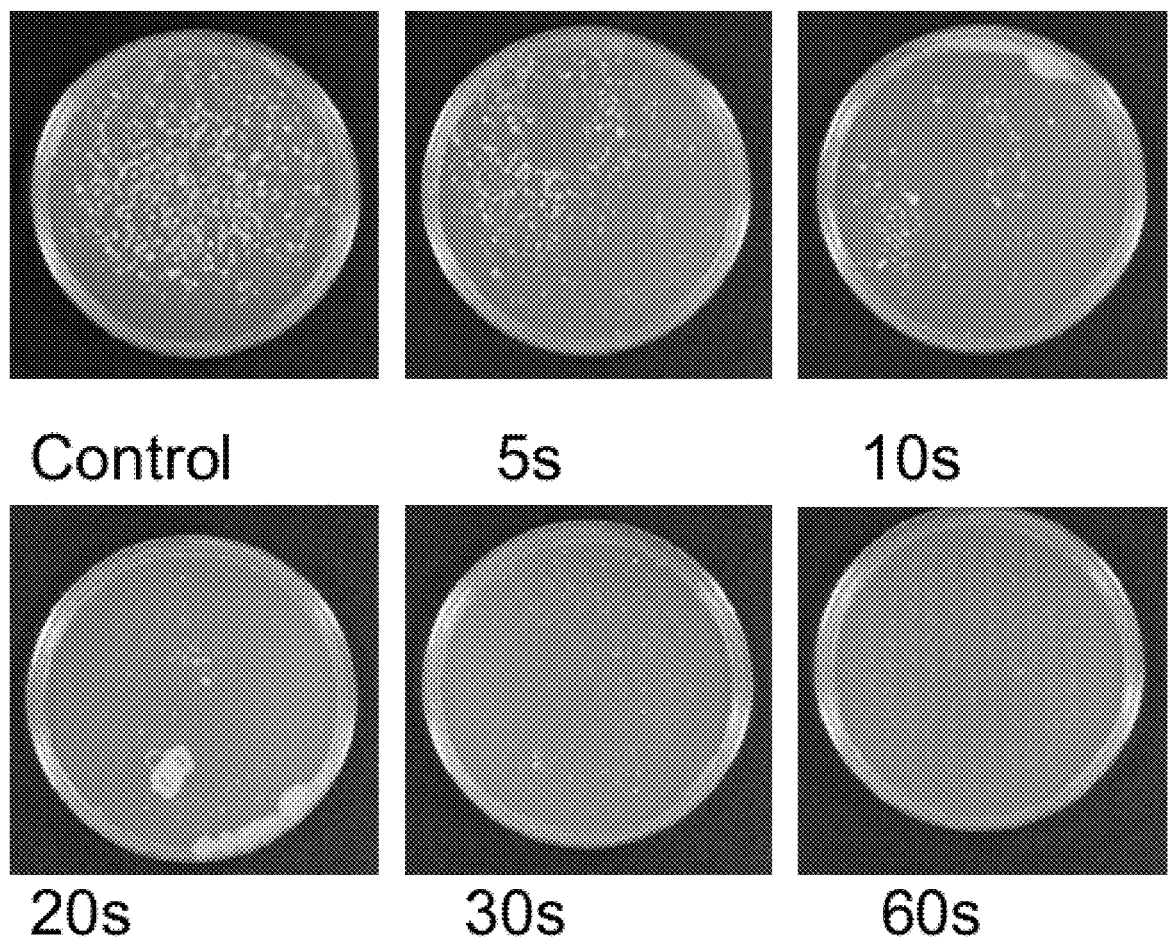
FIG. 7 represents the results of the direct contact experiments for S. cerevisiae experimental groups.

The plasma applicator was pre-sanitized by standard UV sanitation procedures. After coming in contact with a simulated sneeze and generating plasma for a set length of time, the plasma applicator as described above was placed in a covered petri dish directly contacting the surface of a medium consisting of yeast extract peptone dextrose (YEPD). The test target for Experiment 1 was *S. cerevisiae* at a concentration of $3.5 \times 10^8$ unit/mL. There was a total of 6 testing groups (5+1 control), with each testing group corresponding to a different length of time for which plasma was generated (i.e the plasma applicator was active): 5 seconds, 10 seconds, 20 seconds, 30 seconds, and 60 seconds. Results are shown in FIG. 7.

B. Experiment 2-*E. coli*

Figure 8:
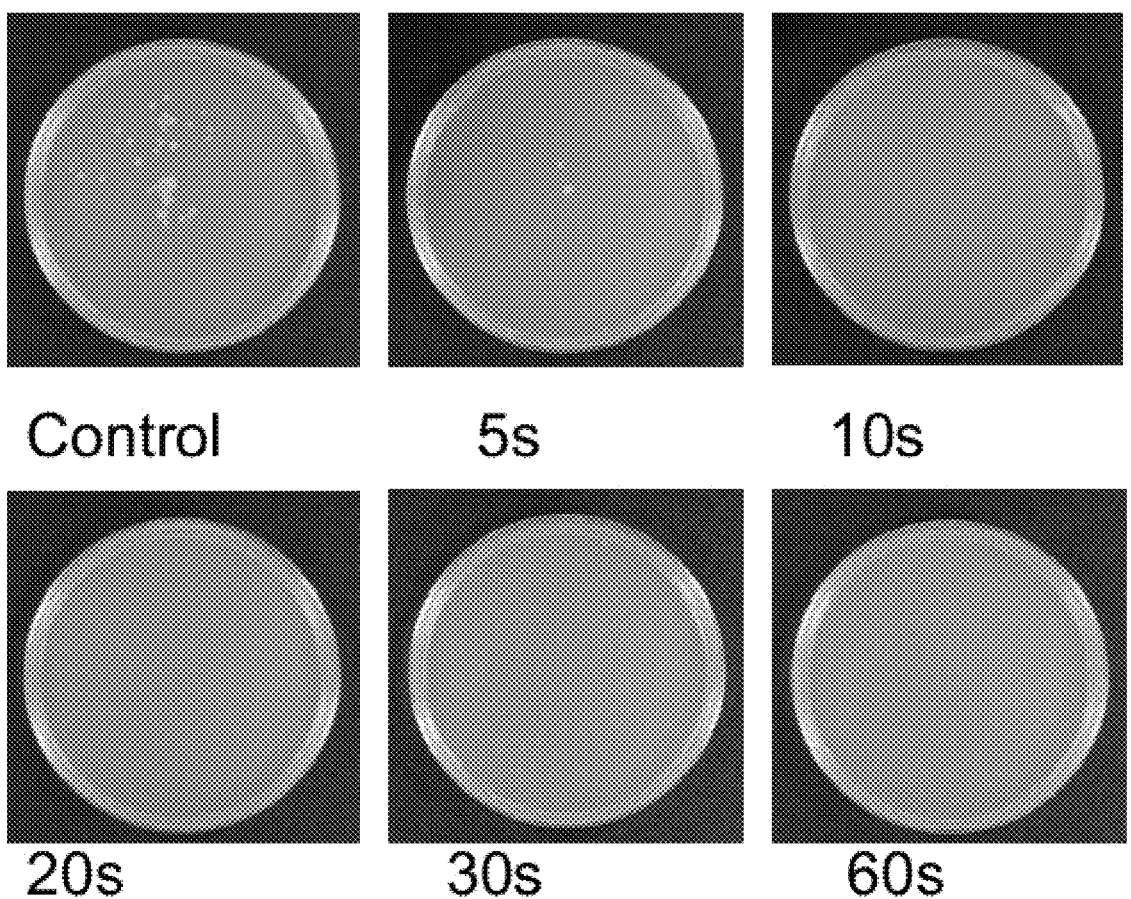
FIG. 8 represents the results of the direct contact experiments for E. coli experimental groups.

The plasma applicator was pre-sanitized by standard UV sanitation procedures. After coming in contact with a simulated sneeze and generating plasma for a set length of time, the plasma applicator as described was placed in a covered petri dish directly contacting the surface of a medium consisting lysogeny broth (LB). The test target for Experiment 2 was *E. coli* at a concentration of $3.6 \times 10^8$ unit/mL. There was a total of 6 testing groups (5+1 control), with each testing group corresponding to a different length of time for which plasma was generated (i.e the plasma applicator was active): 5 seconds, 10 seconds, 20 seconds, 30 seconds, and 60 seconds. Results are shown in FIG. 8.

C. Experiment 3-*S. cerevisiae* With Contamination

Figure 9:
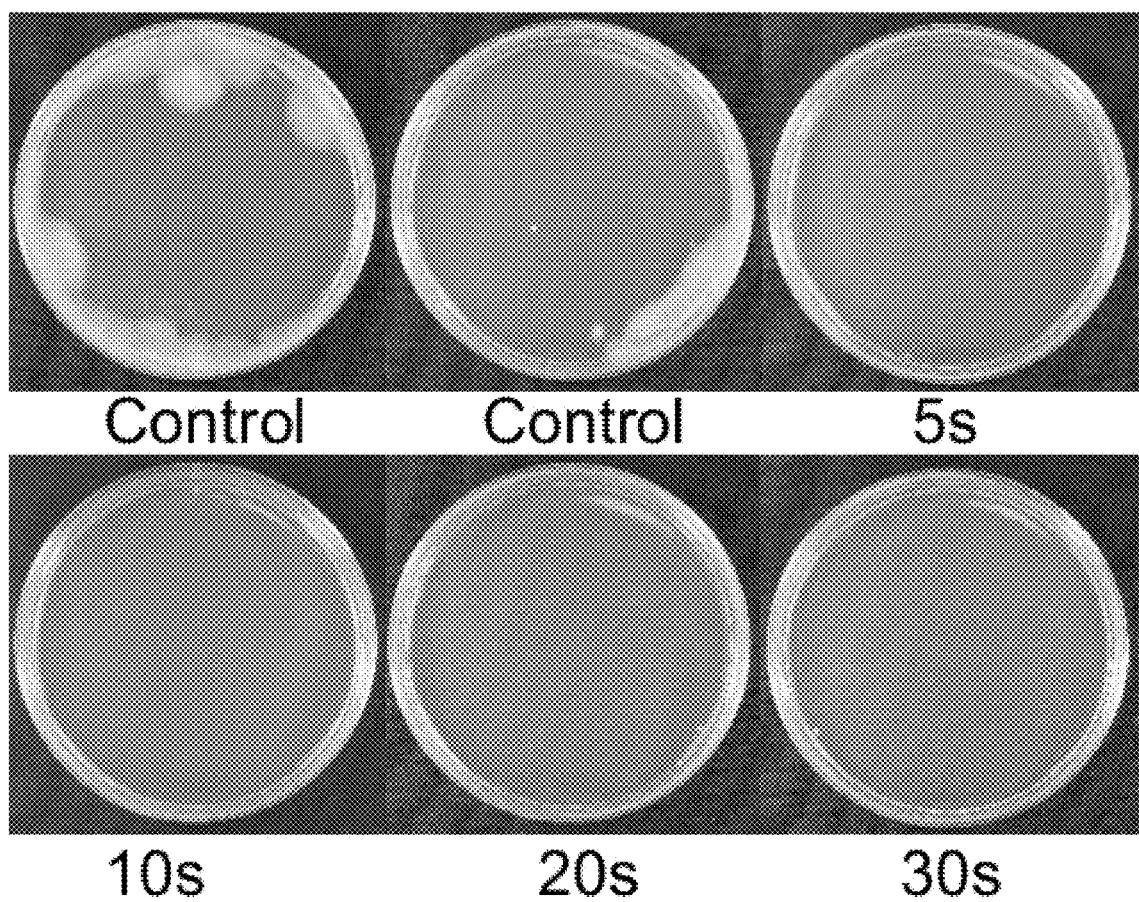
FIG. 9 represents the results of the direct contact experiments for *S. cerevisiae* experimental groups, where the plasma applicator was not disinfected prior to the direct contact.

The plasma applicator was not pre-sanitized by standard UV sanitation procedures (i.e. "with contamination.") After coming in contact with a simulated sneeze and generating plasma for a set length of time, the plasma applicator as described was placed in a covered petri dish directly contacting the surface of a medium consisting of yeast extract peptone dextrose (YEPD). The test target for Experiment 3 was contaminated *S. cerevisiae*. There was a total of 6 testing groups (5+1 control), with each testing group corresponding to a different length of time for which plasma was generated (i.e the plasma applicator was active): 5 seconds, 10 seconds, 20 seconds, 30 seconds, and 60 seconds. Results are shown in FIG. 9. The contamination was later revealed to be *Bacillus*.

D. Experiment 4-*E. coli* With Contamination

Figure 10:
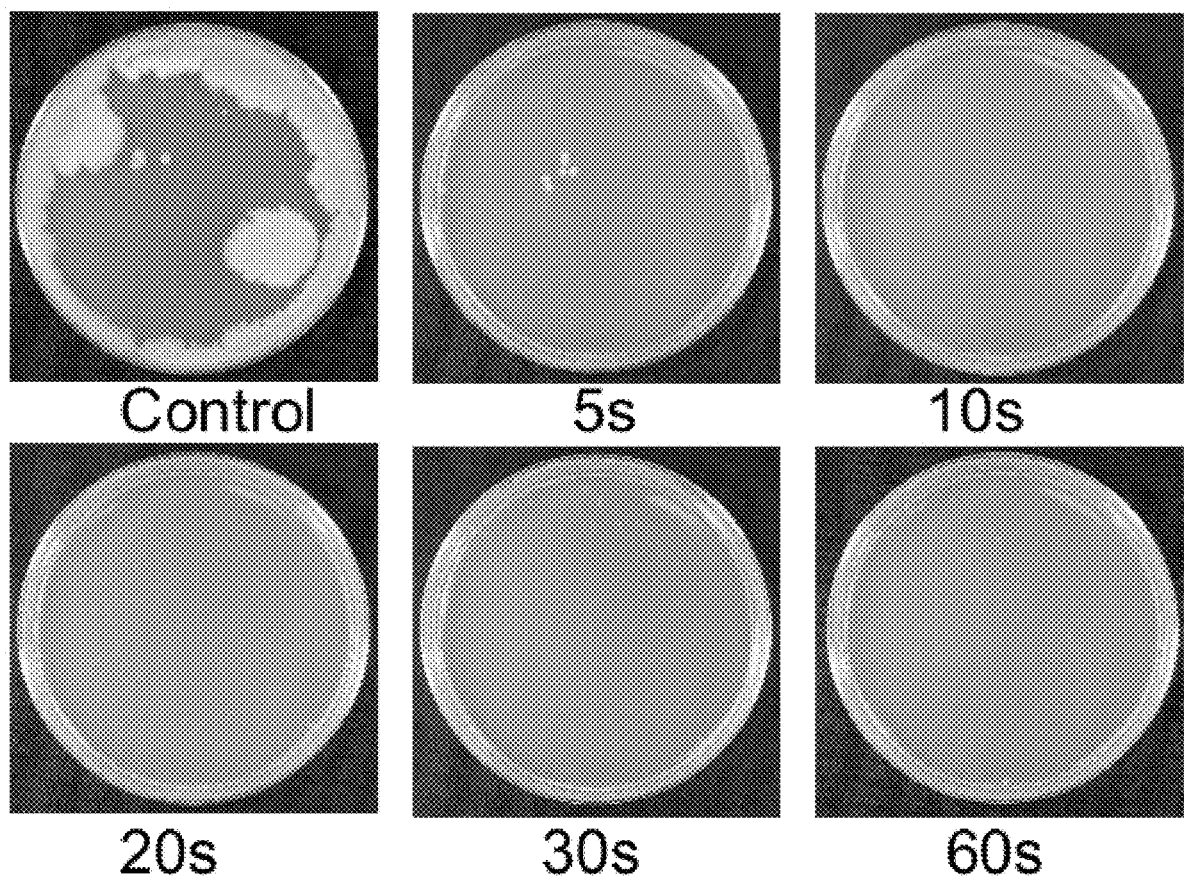
FIG. 10 represents the results of the direct contact experiments for *S. cerevisiae* experimental groups, where the plasma applicator was not disinfected prior to the direct contact.

The plasma applicator was not pre-sanitized by standard UV sanitation procedures (i.e. "with contamination.") After coming in contact with a simulated sneeze and generating plasma for a set length of time, the plasma applicator as described was placed in a covered petri dish directly contacting the surface of a medium consisting of lysogeny broth (LB). The test target for Experiment 4 was contaminated *E. coli*. There was a total of 6 testing groups (5+1 control), with each testing group corresponding to a different length of time for which plasma was generated (i.e the plasma applicator was active): 5 seconds, 10 seconds, 20 seconds, 30 seconds, and 60 seconds. Results are shown in FIG. 10. The contamination was later revealed to be *Bacillus*.

E. Results

Figure 11:
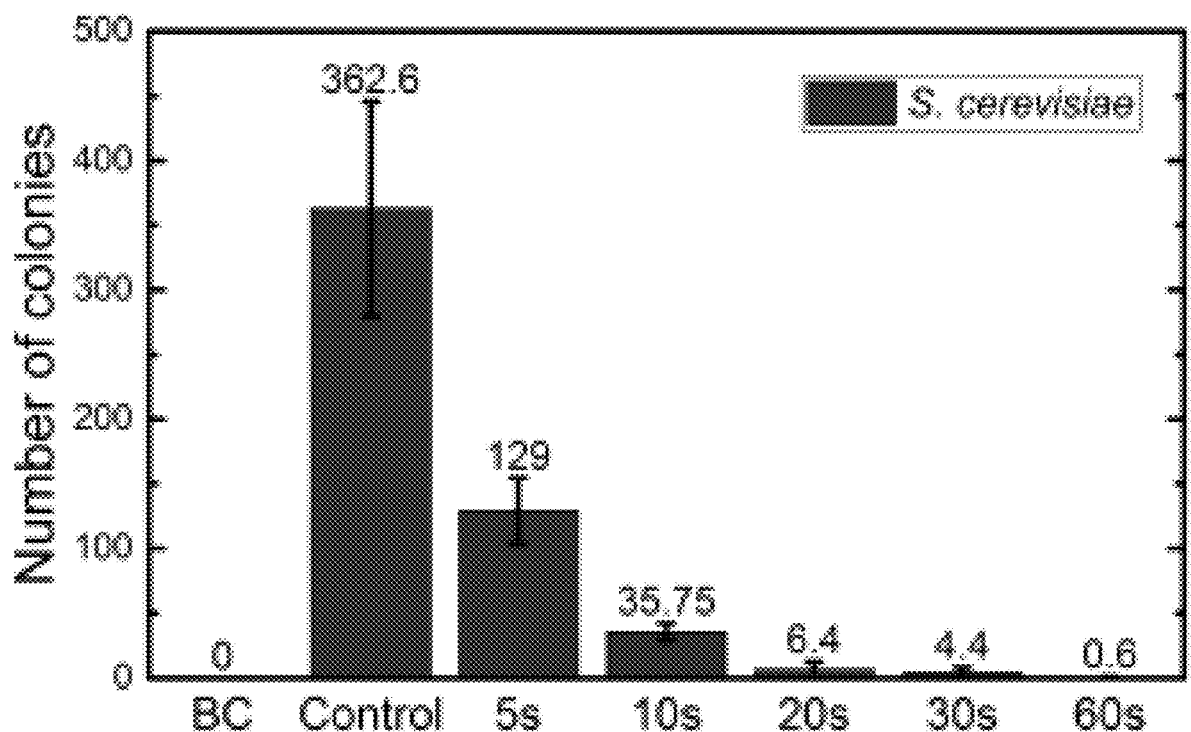
FIG. 11 represents a histogram showing the number of colonies formed by *S. cerevisiae* after being incubated for 48 hours in the direct contact experiments.
Figure 12:
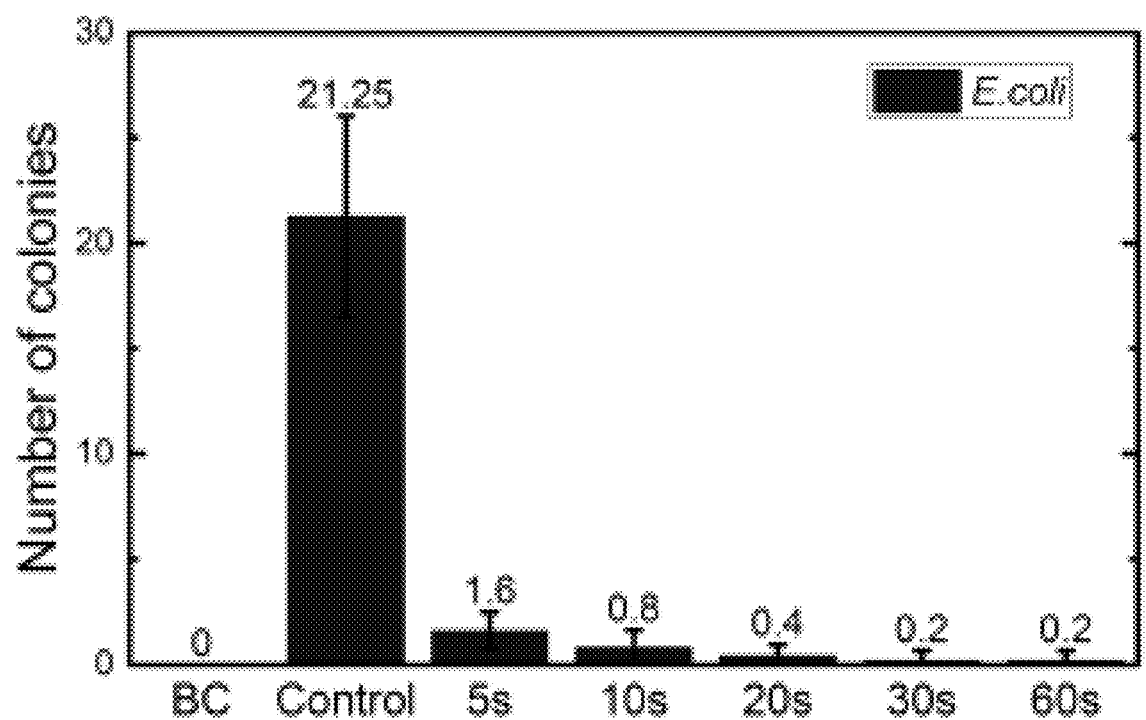
FIG. 12 represents a histogram showing the number of colonies formed by *E. coli* after being incubated for 48 hours in the direct contact experiments.

Quantitative results (histograms) for *S cerevisiae* and *E. coli* are shown in FIG. 11 and FIG. 12. The results indicated that with 60 seconds of plasma treatment, there were no observable cells on the YEPD media. With only 10 seconds of plasma treatment, there were no observable colonies on the LB media.

The substrate layers (metallized paper) of the plasma applicators are not inherently sterile products, thus likely containing contaminants on the surface and within the porous structure. This was the basis behind the "with contamination" testing protocols, as during testing, non-specific contaminants/colonies were observed in those scenarios where the plasma applicator was not pre-sanitized. Notably, however, none of the samples appeared to be contaminated after 30 seconds of active plasma generation. Thus, the results indicate that by generating volume plasma in particular, the plasma applicators self-sanitized by removing the contaminant (*bacillus*) from the fibrous interior of the substrate layers.

4. Self-Sanitizing Touchpads

The plasma applicators of the present invention can be incorporated into self-sanitizing touchpads, e.g. capacitive touchpads. Capacitive touchpads using, for example, metallized paper (an exemplary substrate layer of the present invention), are disclosed in Mazzeo A D, et. al. (2012) Paper-Based, Capacitive Touch Pads., *Adv. Mater* 24(21): 2850-2856, hereby incorporated by reference in its entirety. By integrating plasma applicators of the present invention with capacitive touchpads, these devices are capable of sanitizing themselves after being touched. The operation occurred as follows. A button was touched with two fingers to activate corresponding LEDs as well as activating the plasma to sanitize the buttons with a frequency of 500 Hz and a $V_{p-p}$ of ±2.5 kV. The conductive traces on the touchpad were at least 2.5 mm away from each other, as narrower gaps resulted in discharges and non-uniform ablation of the conductive layer (evaporated aluminum).

5. Paper-Based Disposable Garments

To demonstrate the use of the plasma applicators of the present invention in garment-like systems, a rectangular, paper-based band with half the surface area covered with a hexagonal, conductive layer was prepared. There was no conductive layer on the other half of the band as it was removed via laser ablation. The design thus produced plasma only on the half of the band that contained a conductive layer. The other half was reserved as a control group with Kapton tape attached to the surface.

The paper-based band was wrapped around an individual's wrist and was then sprayed with an atomized suspension of *E. coli* on the surface of the band to ensure approximately equal distribution of the *E. coli*. The concentration of the suspension was calculated as approximately $3\times10^8$ cells/mL. The band was then removed from the individual's wrist and connected to electrodes. The plasma applicator was activated under the excitation of an AC source with peak-peak voltage of ±2.3 kV and a frequency of 1.7 kHz. After activating the plasma applicator, the electrodes were removed and the cells were transferred to the surface of a pre-prepared lysogeny broth (LB) medium. The medium was incubated at 37° C. for 48 hours. From a qualitative perspective, the number of resultant colonies were inversely proportional to the duration of plasma treatment.

6. Kirigami-Like Plasma Generators

A kirigami-based device comprising the plasma applicators of the present invention (utilizing metallized paper as the substrates) was constructed with an initial geometry of a 2-D square. When stretched, it opened into a 3-D structure. An external voltage source was applied to the kirigami device, which resulted in an excitation frequency of 500 Hz while the peak-to-peak voltage was ±2.5 kV.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A plasma applicator consisting of a first substrate layer, a second substrate layer, and an adhesive layer;
    wherein the first substrate layer and the second substrate layer are comprised of a fibrous base layer and a metallic surface layer,
    wherein the adhesive layer binds the fibrous base layer of the first substrate layer to the fibrous base layer of the second substrate layer, wherein the metallic surface layer of the first substrate layer and the metallic surface layer of the second substrate layer is exposed, and
    wherein the metallic surface layer of the first substrate layer and the metallic surface layer of the second substrate are configured to be placed in conductive contact with a high voltage source to generate dielectric barrier discharge (DBD) upon exposure to a high voltage source.

2. The plasma applicator of claim 1, (a) wherein the first substrate layer comprises at least one polymer layer inserted between the fibrous base layer and the metallic surface layer of the first substrate layer; (b) wherein the second substrate layer comprises at least one polymer layer inserted between the fibrous base layer and the metallic surface layer of the second substrate layer; or (c) wherein the first substrate layer comprises at least one polymer layer inserted between the fibrous base layer and the metallic surface layer of the first substrate layer and wherein the second substrate layer comprises at least one polymer layer inserted between the fibrous base layer and the metallic surface layer of the second substrate layer.

3. The plasma applicator of claim 1, wherein the first substrate layer is patterned.

4. The plasma applicator of claim 1, wherein the fibrous base material of at least one of the first substrate layer and the second substrate layer comprises cellulose-based paper.

5. The plasma applicator of claim 4, wherein the metallic surface layer of at least one of the first substrate layer and the second substrate layer comprises vacuum evaporated aluminum.

6. The plasma applicator of claim 5, wherein at least one of the first substrate layer and the second substrate layer comprises metallized paper.

7. The plasma applicator of claim 1, wherein the fiber base material of at least one of the first substrate layer and the second substrate layer is at least partially exposed.

8. The plasma applicator of claim 7, wherein the plasma applicator is capable of generating both surface plasma and volume plasma.

9. A plasma applicator consisting of a first substrate layer, a second substrate layer, an adhesive layer, and a polymer coating layer,
   wherein the first substrate layer and the second substrate layer are comprised of a fibrous base layer and a metallic surface layer,
   wherein the adhesive layer binds the fibrous base layer of the first substrate layer to the fibrous base layer of the second substrate layer and wherein the polymer coating layer is applied to the metallic surface layer of at least one of the first substrate layer and the second substrate layer, and
   wherein the metallic surface layer of the first substrate layer and the metallic surface layer of the second substrate are configured to be placed in conductive contact with a high voltage source to generate dielectric barrier discharge (DBD) upon exposure to a high voltage source.

10. A method of disinfecting a surface comprising directly contacting a surface with the plasma applicator of claim 1.

11. A method of disinfecting a surface comprising indirectly contacting a surface with the plasma applicator of claim 1.

12. The method of claim 11, wherein the indirect contact occurs for ten seconds or less, and wherein at least 95% of contaminants are sanitized.

13. A capacitive touch-based interface incorporating the plasma applicator of claim 1.

14. The method of claim 11, wherein the indirect contact occurs for thirty seconds or less, and wherein at least 99% of contaminants are sanitized.

15. A handheld device comprising the plasma applicator of claim 1, wherein the plasma applicator is in contact with a high voltage source.

16. The plasma applicator of claim 3, wherein the first substrate layer is honeycomb patterned.

17. A package comprising the plasma applicator of claim 1 and a non-conductive spacer attached to an exposed surface of the plasma applicator which is adapted to be placed in contact with contents of said package, and wherein the plasma applicator is placed on an interior surface of the package.

18. The package of claim 17 containing conductive contacts on an exterior surface of the package.

19. A bandage comprising the plasma applicator of claim 1 and a non-conductive spacer on a surface of the plasma applicator which is adapted to be placed on skin tissue.

20. A disposable garment incorporating the plasma applicator of claim 1.

* * * * *